US00PP22345P2

(12) United States Plant Patent
Chen

(10) Patent No.: US PP22,345 P2
(45) Date of Patent: Dec. 13, 2011

(54) *CORDYLINE* PLANT NAMED 'SPRICORHAPSO'

(50) Latin Name: *Cordyline australis*
Varietal Denomination: Spricorhapso

(75) Inventor: Jianping Chen, Zhejiang (CN)

(73) Assignee: Sprint Horticulture Pty. Ltd., Wamberal, New South Wales (AU)

( * ) Notice: Subject to any disclaimer, the term of this patent is extended or adjusted under 35 U.S.C. 154(b) by 0 days.

(21) Appl. No.: 12/804,638

(22) Filed: Jul. 26, 2010

(51) Int. Cl.
*A01H 5/00* (2006.01)

(52) U.S. Cl. ..... Plt./383

(58) Field of Classification Search ..... Plt./383
See application file for complete search history.

(56) References Cited

U.S. PATENT DOCUMENTS

PP19,102 P2 * 8/2008 Rendle ..... Plt./383
PP20,634 P3 * 1/2010 Rendle ..... Plt./383

OTHER PUBLICATIONS

Anonymous. Sprint Horticulture 2010 Product cataog "Design Edge *Cordyline* Rhapsody" p. 5. accessed Jul. 18, 2011.*

* cited by examiner

*Primary Examiner* — Wendy C Haas
(74) *Attorney, Agent, or Firm* — C. A. Whealy

(57) ABSTRACT

A new and distinct cultivar of *Cordyline* plant named 'Spricorhapso', characterized by its upright and outwardly slanting growth habit; vigorous growth habit and relatively rapid growth rate; long lanceolate variegated leaves with brown, greyed red, light orange white-colored longitudinal stripes; tolerance to low and high temperatures; excellent keeping quality and good garden performance.

3 Drawing Sheets

Botanical designation: *Cordyline australis*.
Cultivar denomination: 'SPRICORHAPSO'.

BACKGROUND OF THE INVENTION

The present invention relates to a new and distinct cultivar of *Cordyline* plant, botanically known as *Cordyline australis*, and hereinafter referred to by the name 'Spricorhapso'.

The new *Cordyline* plant is a naturally-occurring whole plant mutation of the *Cordyline australis* 'Red Star', not patented. The new *Cordyline* plant was discovered and selected by the Inventor within a population of plants of 'Red Star' in a controlled greenhouse environment in Zhejiang, China on Apr. 2, 2004.

Asexual reproduction of the new *Cordyline* plant by micropropagated cuttings in Zhejiang, China since April, 2004, has shown that the unique features of this new *Cordyline* plant are stable and reproduced true to type in successive generations.

SUMMARY OF THE INVENTION

Plants of the new *Cordyline* have not been observed under all possible environmental conditions. The phenotype may vary somewhat with variations in environment such as temperature and light intensity, without, however, any variance in genotype.

The following traits have been repeatedly observed and are determined to be the unique characteristics of 'Spricorhapso'. These characteristics in combination distinguish 'Spricorhapso' as a new and distinct cultivar of *Cordyline* plant:

1. Upright and outwardly slanting growth habit.
2. Vigorous growth habit and relatively rapid growth rate.
3. Long lanceolate variegated leaves with brown, greyed red, light orange white-colored longitudinal stripes.
4. Tolerant to low and high temperatures.
5. Excellent keeping quality and good garden performance.

Plants of the new *Cordyline* differ from plants of the parent, 'Red Star', primarily in leaf color as plants of 'Red Star' have dark burgundy red-colored leaves.

Plants of the new *Cordyline* can be compared to plants of the *Cordyline australis* 'Sunrise', disclosed in U.S. Plant Pat. No. 20,634. In side-by-side comparisons conducted in Wamberal, New South Wales, Australia, plants of the new *Cordyline* differed primarily from plants of the 'Sunrise' in the following characteristics:

1. Plants of the new *Cordyline* were more vigorous than plants of 'Sunrise'.
2. Plants of the new *Cordyline* were shorter and broader than plants of 'Sunrise'.
3. Leaves of plants of the new *Cordyline* were more upright than and not as weeping as leaves of plants of 'Sunrise'.
4. Plants of the new *Cordyline* and 'Sunrise' differed in leaf coloration as plants of 'Sunrise' had red and brown-colored leaves.

Plants of the new *Cordyline* can also be compared to plants of the *Cordyline australis* 'Southern Splendour', disclosed in U.S. Plant Pat. No. 19,102. In side-by-side comparisons conducted in Wamberal, New South Wales, Australia, plants of the new *Cordyline* differed primarily from plants of the 'Southern Splendour' in the following characteristics:

1. Leaves of plants of the new *Cordyline* were more upright than and not as weeping as leaves of plants of 'Southern Splendour'.
2. Plants of the new *Cordyline* and 'Southern Splendour' differed in leaf coloration as plants of 'Southern Splendour' had pink and brown-colored leaves.

BRIEF DESCRIPTION OF THE PHOTOGRAPHS

The accompanying photographs illustrate the overall appearance of the new *Cordyline* plant. This photographs show the colors as true as it is reasonably possible to obtain in colored reproductions of this type. Colors in the photographs may differ slightly from the color values cited in the detailed botanical description which accurately describe the colors of the new *Cordyline* plant.

The photograph on the first sheet comprises side and top perspective views of typical plants of 'Spricorhapso' grown in containers.

The photograph on the second sheet is a side perspective view of typical plants of 'Spricorhapso' grown in containers.

The photograph on the third sheet is a top perspective view of typical plants of 'Spricorhapso' grown in containers.

DETAILED BOTANICAL DESCRIPTION

The aforementioned photographs and following observations and measurements describe plants grown during the winter in 14-cm containers in an outdoor nursery in Wamberal, New South Wales, Australia and under conditions and practices which approximate those generally used in commercial *Cordyline* plant production. During the production of the plants, day temperatures ranged from 14° C. to 35° C., night temperatures ranged from 5° C. to 22° C. and light levels averaged 100,000 lux. Plants were one year old when the photographs and the botanical description were taken. In the following description, color references are made to The Royal Horticultural Society Colour Chart, 2007 Edition, except where general terms of ordinary dictionary significance are used.

Botanical classification: *Cordyline australis* 'Spricorhapso'.

Parentage: Naturally-occurring whole plant mutation of *Cordyline australis* 'Red Star', not patented.

Propagation:

- *Type.*—By micropropagated cuttings.
- *Time to initiate roots, summer.*—About two weeks at 25° C. to 35° C.
- *Time to initiate roots, winter.*—About three weeks at 18° C.
- *Time to produce a rooted young plant, summer.*—About three months at 25° C.
- *Time to produce a rooted young plant, winter.*—About four months at 18° C.
- *Root description.*—Medium thickness, fibrous, fleshy; white in color.
- *Rooting habit.*—Freely branching; dense.

Plant description:

- *Plant and growth habit.*—Upright and outwardly slanting plant habit; broadly inverted triangle; non-branching habit; vigorous growth habit; relatively rapid growth rate.
- *Plant height.*—About 30 cm.
- *Plant diameter or spread.*—About 50 cm.

Foliage description:

- *Orientation.*—Initially erect to outwardly slanting.
- *Arrangement.*—Whorled; sessile.
- *Length.*—About 25 cm.
- *Width.*—About 1.4 cm.
- *Shape.*—Lanceolate.
- *Apex.*—Acute.
- *Margin.*—Entire.
- *Texture, upper and lower surfaces.*—Leathery; smooth, glabrous.
- *Venation pattern.*—Parallel.
- *Color.*—Developing leaves, upper and lower surfaces: Central longitudinal stripes, close to 200A to 200B to N200A; towards the margins, longitudinal stripes close to 180A. Fully expanded leaves, upper surface: Central longitudinal stripes, close to 200A to 200B to N200A; random central longitudinal streaks, close to 180A to 180B; towards the margins, longitudinal stripes close to 180A to 180B; at the apical margins, close to 180C; along the central and basal margins, close to 159B; with development, central longitudinal stripes and streaks become closer to 194A, 65A and 148B. Fully expanded leaves, lower surface: Longitudinal stripes, close to 180B with random longitudinal striations, close to 186B and 200A to 200B; with development, colors become closer to 177B, 185D and 200B. Venation, upper and lower surfaces: Similar to surface coloration.

Flower description: Flower initiation and development has not been observed on plants of the new *Cordyline*.

Disease/pest resistance: Plants of the new *Cordyline* have not been shown to be resistant to pathogens and pests common to *Cordyline*.

Keeping quality: Excellent keeping quality; plants of the new *Cordyline* are durable and will maintain good leaf substance indefinitely.

Garden performance: Plants of the new *Cordyline* have been observed to have good garden performance and to tolerate wind, rain and temperatures ranging from about 1° C. to about 45° C.

It is claimed:

1. A new and distinct *Cordyline* plant named 'Spricorhapso' as illustrated and described.

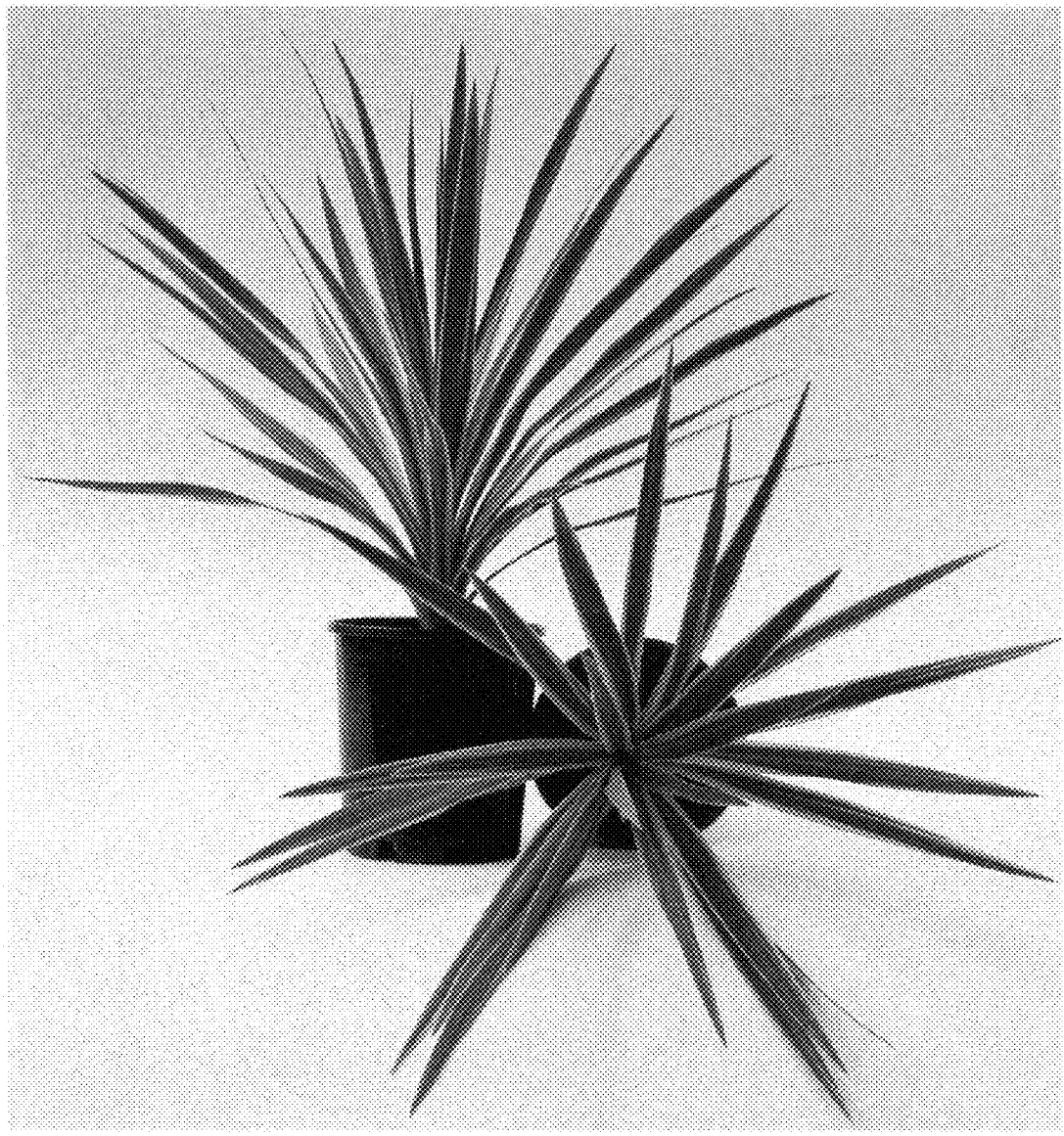

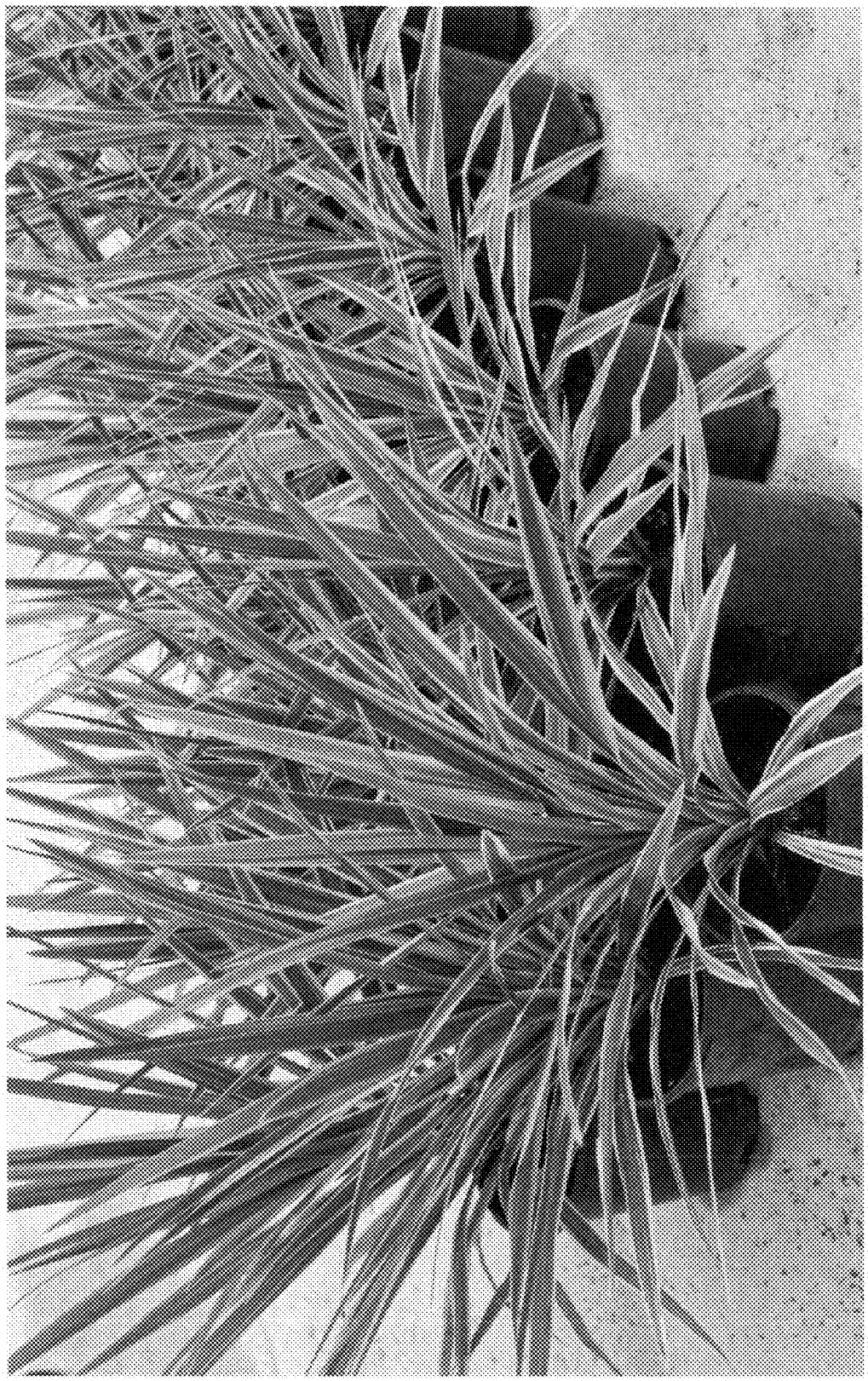

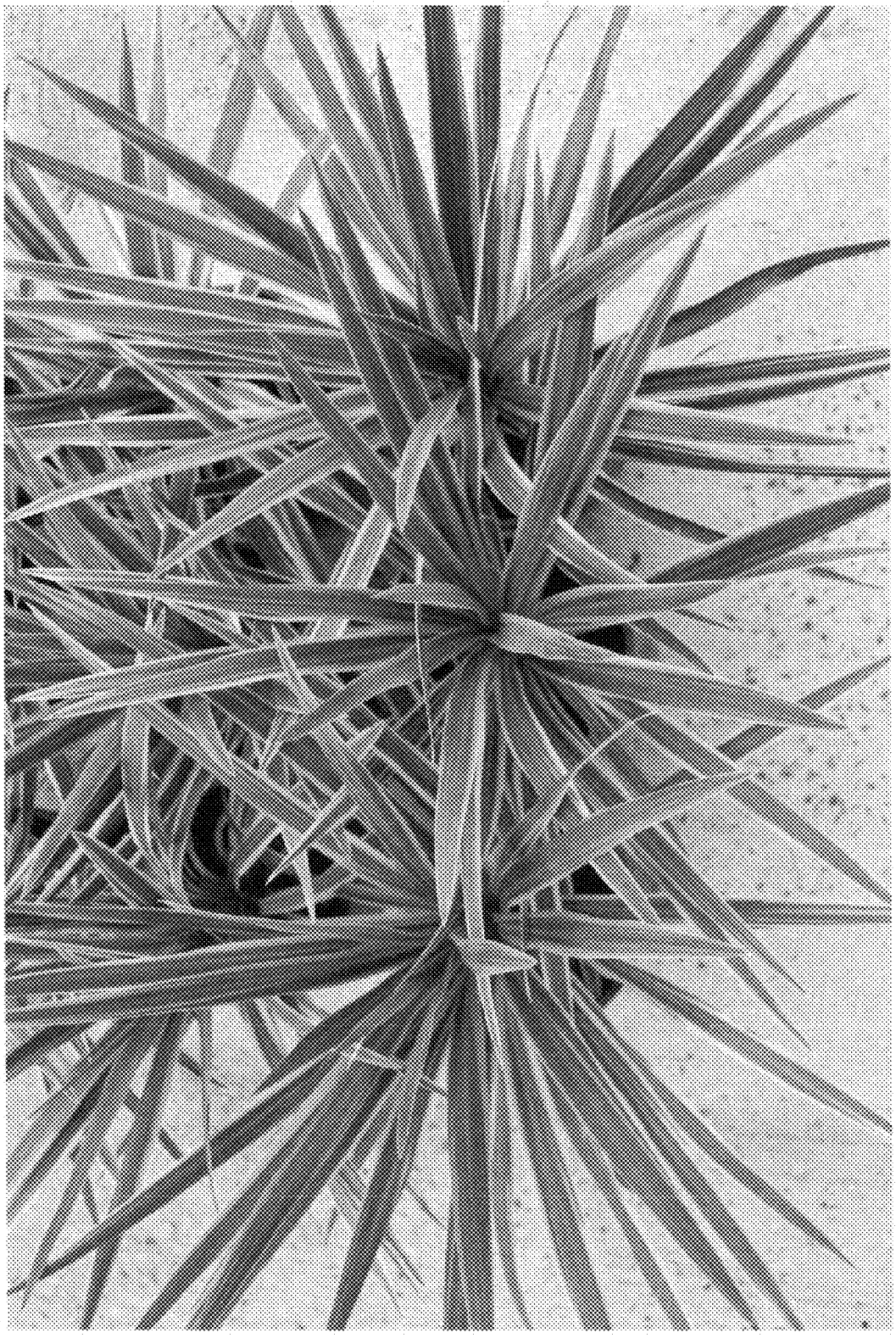

* * * * *